US008642028B2

(12) United States Patent
Perricaudet et al.

(10) Patent No.: US 8,642,028 B2
(45) Date of Patent: Feb. 4, 2014

(54) RECOMBINANT ADENOVIRUSES ENCODING THE SPECIFIC IODINE TRANSPORTER (NIS)

(75) Inventors: Michel Perricaudet, Escrosnes (FR); Martin Schlumberger, Boulogne-Billancourt (FR); Patrice Yeh, Gif sur Yvette (FR); Anne Boland-Auge, L'Hay-les-Roses (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 13/540,421

(22) Filed: Jul. 2, 2012

(65) Prior Publication Data

US 2012/0269773 A1 Oct. 25, 2012

Related U.S. Application Data

(63) Continuation of application No. 12/567,076, filed on Sep. 25, 2009, now abandoned, which is a continuation of application No. 10/018,273, filed as application No. PCT/FR00/01594 on Jun. 8, 2000, now abandoned.

(30) Foreign Application Priority Data

Jun. 11, 1999 (FR) ....................................... 99 07449

(51) Int. Cl.
*A61K 35/76* (2006.01)
(52) U.S. Cl.
USPC ....................................................... 424/93.2
(58) Field of Classification Search
None
See application file for complete search history.

(56) References Cited

U.S. PATENT DOCUMENTS

| 4,814,470 | A | | 3/1989 | Colin et al. |
| 4,857,653 | A | | 8/1989 | Colin et al. |
| 4,924,011 | A | | 5/1990 | Denis et al. |
| 5,290,957 | A | | 3/1994 | Correa et al. |
| 5,292,921 | A | | 3/1994 | Correa et al. |
| 5,438,072 | A | | 8/1995 | Bobee et al. |
| 5,587,493 | A | | 12/1996 | Bouchard et al. |
| 5,652,224 | A | * | 7/1997 | Wilson et al. ............... 514/44 R |
| 6,022,708 | A | | 2/2000 | Sauvage et al. |
| 2010/0080775 | A1 | | 4/2010 | Perricaduet et al. |

FOREIGN PATENT DOCUMENTS

| EP | 0 253 738 | 1/1988 |
| WO | WO 91/17976 | 11/1991 |
| WO | WO 93/00926 | 1/1993 |
| WO | WO 93/00929 | 1/1993 |
| WO | WO 94/26914 | 11/1994 |
| WO | WO 94/28152 | 12/1994 |
| WO | WO 94/29446 | 12/1994 |
| WO | WO 95/02697 | 1/1995 |
| WO | WO 95/03400 | 2/1995 |
| WO | WO 95/27071 | 10/1995 |
| WO | WO 96/01815 | 1/1996 |
| WO | WO 96/10088 | 4/1996 |
| WO | WO 96/22378 | 7/1996 |
| WO | WO 96/25506 | 8/1996 |
| WO | WO 99/43828 | 9/1999 |
| WO | WO 99/60144 | 11/1999 |
| WO | WO 00/12738 | 3/2000 |

OTHER PUBLICATIONS

Mandell et al. (Cancer Research, Feb. 1999, vol. 59, p. 661-668).*
Hidaka et al. (Thyroid, 1996, vol. 6, p. 23-28).*
U.S. Office Action dated Dec. 8, 2011 from U.S. Appl. No. 12/567,076.
U.S. Final Office Action dated Jun. 3, 2011 from U.S. Appl. 12/567,076.
Paire A. et al., "Characterization of the Rat Thyroid Iodide Transporter Using Anti-Peptide Antibodies", *Journal of Bio. Chem.* 272(29):18425-18249 (Jul. 18, 1997).
Lieber A. et al., "Recombinant Adenoviruses with Large Deletions Generated by Cre-Mediated Excision Exhibit Different Biological Properties Compared with First-Generation Vectors In Vitro and In Vivo", *Journal of Virology* 70(12):8944-8960 (Dec. 1996).
Kroughliak V. et al., "Development of Cell Lines Capable of Complementing E1, E4, and Protein IX Defective Adenovirus Type 5 Mutants", *Human Gene Therapy* 6:1575-1586 (Dec. 1995).
Hanahan D., "Heritable Formation of Pancreatic Beta-Cell Tumours in Transgenic Mice Expressing Recombinant Insulin/Simian Virus 40 Oncogenes", *Nature* 315:115-122 (May 9, 1985).
Dai G. et al., "Cloning and Characterization of the Thyroid Iodide Transporter", *Nature* 379:458-460 (Feb. 1996).
Ghosh-Choudbury G. et al., "Human Adenovirus Cloning Vectors Based on Infectious Bacterial Plasmids", *Gene* 50:161-171 (1986).
Maxon H.R. et al., "Relation Between Effective Radiation Dose and Outcome of Radioiodine Therapy for Thyroid Cancer", *NEJM* 309(16) (Oct. 20, 1983).
Cho J-Y et al., "Expression and Activity of Human $Na^+$ /1-Symporter in Human Glioma Cells by Adenovirus-Mediated Gene Delivery (Abstract XP2155151)", *Gene Therapy* 7:740-749 (May 2000).
Chroboczek J. et al., "The Sequence of the Genome of Adenorivus Type 5 and its Comparison with the Genome of Adenovirus Type 2", *Virology* 186:1-13 (1992).
Crouzet J. et al., "Recombinational Construction in *Escherichia coli* of Infectious Adenoviral Genomes", *Proc. Natl. Acad. Sci. USA* 94:1414-1419 (Feb. 1997).
Nemunaitis J. et al., "Phase I Trial of Interferon-γ (IFN-γ) Retroviral Vector Administered Intratumorally to Patients with Metastactic Melanoma", *Cancer Gene Therapy* 6(4):322-330 (1999).
Mandell R., "Gene Therapy of Cancer by Retroviral Transfer and Expression of the Rate Sodium/Iodide Symporter (NIS)", *8th Annual Meeting of the American Association for Cancer Research*, San Diego, CA, USA 38:381 (Apr. 12-16, 1997).
Levero M. et al., "Defective and Nondefective Adenovirus Vectors for Expressing Foreign Genes In Vitro and In Vivo", *Gene* 101:195-202 (1991).

(Continued)

*Primary Examiner* — Agnieszka Boesen
(74) *Attorney, Agent, or Firm* — Scully, Scott, Murphy & Presser, P.C.

(57) ABSTRACT

The present invention relates to the field of gene therapy and the treatment of tumors.

7 Claims, 7 Drawing Sheets

(56) References Cited

OTHER PUBLICATIONS

Figure 1:
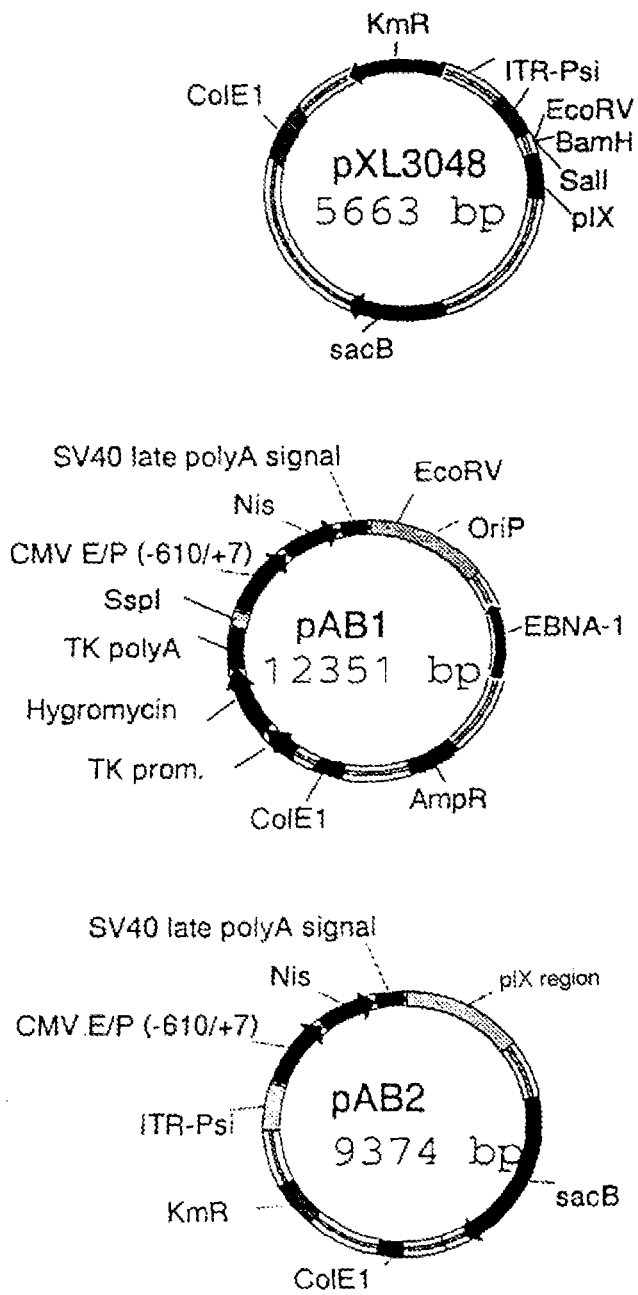

Boshart M. et al., "A Very Strong Enhancer is Located Upstream of an Immediate Early Gene of Human Cytomegalovirus", *Cell 41*:521-530 (Jun. 1985).

Levy O. et al., "N-Linked Glycosylation of the Thyroid $Na^+$/I-Symporter (NIS)", *Journal of Bio. Chem. 273*:22657-22663 (Aug. 28, 1998).

Smanik P.A. et al., "Cloning of the Human Sodium Iodide Symporter", *Biochemical and Biophysical Research Communications* pp. 339-345 (1996).

Yeh P. et al., "Efficient Dual Transcomplementation of Adenovirus E1 and E4 Regions from a 293-Derived Cell Line Expressing a Minimal E4 Functional Unit", *Journal of Virology 70*(1):559-565 (Jan. 1996).

Van Der Vliet P.C. et al., "Thermolabile DNA Binding Proteins from Cells Infected with a Temperature-Sensitive Mutant of Adenovirus Defective in Viral DNA Synthesis", *Journal of Virology 15*(2):348-354 (Feb. 1975).

Myers R.M., "Human STSs", *unpublished*, pp. 1-2 (1997).

Endo T. et al., "Thyroid Transcription Factor-1 Activates the Promoter Activity of Rat Thyroid $Na^+$/I-Symporter Gene", *Molecular Endocrinology 11*:1747-1755 (1997).

Parks R.J. et al., "A Helper-Dependent Adenovirus Vector System: Removal of Helper Virus by Cre-Mediated Excision of the Viral Packaging Signal", *Proc. Natl. Acad. Sci. USA 93*:13565-13570 (Nov. 1996).

Weiss S.J. et al., "Iodide Transport in a Continuous Line of Cultured Cells from Rat Thyroid", *Endocrinology 114*(4):1090-1098 (1984).

U.S. Office Action dated Nov. 29, 2010 from U.S. Appl. No. 12/567,076.

Mandell R.B. et al., "Radioisotope Concentrator Gene Therapy Using the Sodium/Iodide Symporter Gene", *Cancer Research 59*:661-668 (Feb. 1, 1999).

Hidaka Y. et al., "Expression of Thyroid Peroxidase in EBV-Transformed B Cell Lines Using Adenovirus", *Thyroid 6*:23-28 (1996).

International Search Report dated Jan. 9, 2001 received from the European Patent Office from related International Application No. PCT/FR00/01594.

\* cited by examiner

RECOMBINANT ADENOVIRUSES ENCODING THE SPECIFIC IODINE TRANSPORTER (NIS)

CROSS REFERENCE TO RELATED APPLICATIONS

This application is a continuation of U.S. application Ser. No. 12/567,076 filed Sep. 25, 2009, which is a continuation of U.S. application Ser. No. 10/018,273 filed Aug. 7, 2002, which is a 371 of PCT/FR00/01594 filed Jun. 8, 2008, which claims priority of French Patent Application No. 9907449 filed Jun. 11, 1999, the entire contents of which are incorporated herein by reference.

The present invention relates to the field of gene therapy and the treatment of tumors. The invention relates more particularly to the introduction of a gene encoding the specific iodine transporter (Na$^+$/I$^-$ Symporter) NIS into tumor cells by means of an adenoviral vector in order to promote the accumulation of iodine in these cells. The invention also relates to the replication-defective recombinant adenoviruses comprising the nis gene and the use of these vectors in a method for treating cancers combining the transfer of the nis gene into tumor cells and metabolic radiotherapy with iodine-131.

Iodine-131 has been used for more than fifty years in the treatment of differentiated thyroid cancers. Its therapeutic efficacy is linked to the radiation dose delivered to the tumor tissue. For example, in the case of metastases, a tumor response after treatment with iodine-131 is observed when the dose delivered to the tumor tissue is greater than 80 grays whereas the level of tumor response is low or zero for doses of less than 35 grays [Maxon, NEJM, 309:937-941, 1983]. It is possible to generally estimate that the total doses necessary to treat or to reduce the volume of a tumor vary between 40 and 60 grays according to their radiosensitivity. This total dose may be delivered over several treatments with iodine-131, as is carried out during the treatment of fixed metastases of differentiated thyroid cancer.

The radiation dose delivered to the tumor tissue depends on two biological factors: the effective half-life ($T_{eff}$) of iodine-131 in the tumor tissue and the radioactive concentration.

The effective half-life ($T_{eff}$) of iodine-131 in the tumor tissue depends on the biological half-life ($T_{biol}$) and the physical half-life ($T_{phys}$) according to the relationship $1/T_{eff}=1/T_{biol}+1/T_{phys}$. The biological half-life ($T_{biol}$) of iodine-131 in the fixed cells depends on their capacity for organification of iodine. In the absence of organification, as for example in nonthyroid cells, the biological half-life is short, of a few hours to a few tens of hours. The physical half-life ($T_{phys}$) of iodine-131 is 8.02 days. Thus, at best, it is possible to estimate that the effective half-life of iodine-131 in a tumor tissue is a few hours to a few tens of hours.

The radioactive concentration is the ratio between the overall fixing of iodine-131 by the tumor tissue and the mass of this tissue.

By way of example, for an iodine fixing of 0.1% of the activity administered per 1g of tissue and an effective half-life of 1.5 days, it is possible to estimate that the administration of 3.7 gigabecquerel (or 100mCi) delivers a dose of 30 grays to the tumor tissue.

The overall fixing of iodine-131 is a parameter which depends, on the one hand, on the activity of the iodine-131 administered to the patient and, on the other hand, on the capacities of the tumor tissue to concentrate the iodine-131.

The maximum activity of iodine-131 which can be administered to a patient is limited by the iodine toxicity of iodine-131 resulting from the irradiation doses delivered to healthy tissues and in particular to the bone marrow. Thus, in the case of thyroid cancer, the therapeutic activities administered, while the patients are in a state of hypothyroidism, are generally between 3.7 and 10 GBq (100 to 300 mCi). The maximum activities which can be administered to euthyroid patients are higher because the retention of iodine is then twice as low as that observed in the case of hypothyroidism; they reach values of between 8.5 and 22.2 GBq (500 to 600 mCi).

The capacity of normal tissue to concentrate iodine-131, for a given activity administered to the patient, depends on the level of expression of the iodine symporter and its biological activity. This was demonstrated by the study of normal and pathological human thyroid tissues and by in vitro studies of the NIS activity. The specific activity of iodine-131 being high, no saturation phenomenon with increase in the activity of iodine-131 administered was observed.

Because of the limitation of the maximum activity of iodine-131 which can be administered to the patient, it would be desirable to be able to increase the capacity of the tumor tissue to concentrate iodine-131 in order to increase the overall fixing of iodine-131.

It is also critical that the increase in the fixing of iodine occurs homogeneously in the tumor tissue. Indeed, the fixing of iodine in a fixing tissue may be very heterogeneous from one cell to another, or even from one tumor region to another. The irradiation dose in the tumor tissue is essentially delivered by the β emission of iodine-131. However, its path in biological tissues is at most 2 to 3 mm. Furthermore, around a localized source, the irradiation dose decreases exponentially with distance. These elements reinforce the importance of reaching a high radioactive concentration in the fixing tumor regions and, on the other hand, the need to obtain a fixing of iodine which is as homogeneous as possible.

It should be noted that the fixing of iodine-131 by the human thyroid, and therefore its irradiation, can be easily suppressed (unmeasurable fixing of iodine-131) by the administration of L-triiodothyronine 1 µg/kg/day divided into three daily doses for three weeks.

The NIS transporter is responsible for the concentration of circulating iodine (in the form of iodide I$^-$) by the thyreocytes [for a review see P. Thomopoulos, Médecine et Science, vol 4 (10), p. 825-828]. The concentration of iodine in these cells exhibits the following characteristics: the iodine is concentrated by a factor of 30 to 40 fold against an electrochemical gradient; it requires the presence of sodium (Na$^+$); this involves active transport; it is competitively inhibited by certain anions, such as thiocyanate, perchlorate, pertechnetate. The concentration of iodine by the thyreocytes is followed by the organification of the iodine and the synthesis of iodotyrosines and of thyroid hormones (thyroxine T4 and triiodothyronine T3).

The genes encoding the murine transporter [Dai et al. Nature 379: 458-460 (1996)] and the human transporter [Smanik P. A. et al. Biochem. Biophys. Res. Commun. 226: 339-345 (1996)] of NIS iodine have been isolated; they are 84% identical. The gene is located on chromosome 19p in the human species. It comprises 15 exons separated by 14 introns. Its transcription gives rise to two forms by alternative splicing, of which the long form predominates in the thyroid. The protein has a molecular weight of 55 kDa, reaching 80 kDa after glycosylation. It is located in the laterobasal membrane of the thyreocytes. Its amino-terminal and carboxy-terminal ends are intracellular while the remainder of the peptide chain comprises 13 transmembrane segments joined by intracellular and extracellular loops [Levy et al., 1998. J. Biol. Chem. 273: 22657-22663]. The introduction of the gene encoding NIS into nonthyroid cells confers on them the capacity to capture iodine, with the same properties as the thyreocytes, in particular the necessary presence of sodium ($Na^+$) and the inhibition by perchlorate anions.

The transcription of the nis gene is activated in the thyreocytes by TSH. This effect is mediated by cyclic AMP. The half-life of the protein, in the murin thyreocytes is 4 days [Paire A. et al. J. Biol. Chem. 272: 18245-18249 (1997)]. In the extrathyroid tissues, the activity of the gene is lower than that of the thyroid in the basal state. This is presumably due to the stimulation of the transcription of the nis gene in the thyreocytes, by the specific transcription factor TTF-1 (thyroid transcription factor 1), which can bind to the promoter of the thyroid nis gene, but not to that of other tissues [Endo T. et al. Mol. Endocrinol. 11: 1747-1755 (1997)]. Apart from the thyroid, certain tissues are capable of capturing and of concentrating iodine, in particular the salivary glands and the gastric mucous membrane.

A recent study reports the transfer of the nis gene by means of a retroviral vector into human or murine tumor cells [Mandell et al. Cancer Research 59: 661-668 (1999)]. These results are of interest in that they show that it is possible to express the nis gene in nonthyroid cells and to observe concentration of iodine in cells which do not naturally accumulate this element. However, a number of limiting factors remain to be overcome in order to reach a sufficient level of fixing of iodine to envisage a therapeutic application.

A first factor is the low level of expression of the nis gene in tumor cells. For example, in the abovementioned study, the results obtained in vitro show that the concentration of iodine reached in nonthyroid tumor cells remains approximately twice as low as the iodine concentration accumulated in the thyroid cells.

Furthermore, taking into account the large disruptions which tumor cells exhibit at the membrane level, it appears difficult to ensure the functional integration of a transporter with an efficacy comparable to that of nontumor thyroid cells.

Another limiting factor is the absence of organification of iodine in nonthyroid cells; yet this organification of iodine is a necessary component for maintaining iodine in the cells. Thus, in the study reported above, a very rapid efflux of the iodine accumulated in vitro (between 30 and 60 min) is observed for nonthyroid cells.

Finally, taking into account the heterogeneity of the tumor cells and of the large modifications of these cells at the membrane level, it appears difficult to be able to reach a homogeneous distribution of the NIS transporter in the membranes of tumor cells.

Thus, no approach described now has yet made it possible to reach an accumulation of iodine in the nonthyroid tumor with a sufficient level of expression to envisage the use of iodine-131 for the treatment of nonthyroid tumors.

The present invention presents an improved method of treating tumors combining gene therapy and radiotherapy with iodine-131.

The present invention describes in particular a method which makes it possible to increase the efficacy of the fixing of iodine at the level of nonthyroid tumors and which thus makes it possible to apply to the nonthyroid tumors the principles of radiotherapy successfully developed for the treatment of thyroid cancers.

The present invention results from the demonstration that the transfer of the gene encoding the specific iodine transporter ($Na^+/I^-$ Symporter) NIS by means of a defective recombinant adenovirus makes it possible to reach a very high accumulation of iodine in nonthyroid tumor cells. In a specific embodiment, the supply of a defective adenovirus expressing the nis gene makes it possible to accumulate iodine at concentrations about five times as high as those observed in thyroid cells. This surprising capacity of nonthyroid tumor cells to accumulate iodine-125 makes it possible to envisage for this type of tumors a novel therapeutic approach based on metabolic radiotherapy with iodine-131, which approach was up until now reserved for the treatment of certain thyroid tumors.

The major benefit of metabolic radiotherapy is to deliver large irradiation doses to tissues fixing the radioactive isotope, without significantly irradiating the surrounding tissues.

The discovery that it is effectively possible to substantially concentrate iodine in tumor cells which are normally incapable of accumulating this element makes it possible to envisage the application of this method in numerous indications for the treatment of tumors of nonthyroid origin. Two types of indications are more particularly envisaged: tumors which are hardly accessible to external radiotherapy because of their location; by way of example, there may be mentioned inoperable prostate cancers or intracerebral tumors; tumors which have already been irradiated and for which additional external radiotherapy is impossible because the maximum doses have already been administered: this relates to all cancers occurring or relapsing in irradiated regions. This method is also applicable to the treatment of thyroid tumors which have lost the capacity to capture iodine and which do not respond to metabolic therapy.

It is also possible to envisage combining metabolic radiotherapy and external radiotherapy as is carried out in the case of metastases of differentiated thyroid cancer. This combination makes it possible to increase the therapeutic efficacy of the radiotherapy without increasing toxicity. This combination appears particularly advantageous for tumors which are not very sensitive to radiotherapy. Moreover, it makes it possible to envisage the application of this technique to tumors which would not be accessible to metabolic radiotherapy alone, because of their excessively large size.

A first subject of the invention therefore consists in a defective recombinant adenovirus comprising at least one heterologous DNA sequence encoding the specific iodine transporter ($Na^+/I^-$ Symporter) NIS, or one of its derivatives.

For the purposes of the present invention, the expression "derivative" of the specific iodine transporter ($Na^+/I^-$ Symporter) NIS is understood to mean any analogue, fragment or mutated form which is derived from the NIS polypeptide and which retains a specific iodine transporting activity. Various derivatives may exist in the natural state. These derivatives may be allelic variations characterized by differences in the nucleotide sequence of the structural genes encoding NIS or may result from differential splicing or post-translational modifications. These derivatives may be obtained by substitution, deletion, addition and/or modification of one or more amino acid residues. These modifications may be carried out by any techniques known to persons skilled in the art. These derivatives are in particular molecules having a higher affinity for their substrates, sequences allowing improved expression in vivo, molecules exhibiting greater resistance to proteases, molecules having greater biological efficacy or fewer side effects, or possibly novel biological properties. Other derivatives which may be used in the context of the invention are in particular molecules in which one or more residues have been substituted, derivatives obtained by deletion of regions not or not greatly involved in the interaction with the binding sites considered or expressing undesirable activity, and derivatives comprising additional residues relative to the native sequence, such as for example a secretory signal and/or a joining peptide.

The specific iodine transporter (Na+/I− Symporter) NIS or its derivative, which is produced in the context of the present invention, may be a cDNA, a genomic DNA (gDNA), or a hybrid construct consisting, for example, of a cDNA into which one or more introns would be inserted. It may also include synthetic or semi-synthetic sequences. Advantageously, a cDNA or a gDNA is used. In particular, the use of a gDNA may allow better expression in human cells.

According to a first embodiment, it is a cDNA sequence encoding the specific iodine transporter (Na+/I− Symporter) NIS of murine origin. According to a preferred embodiment of the invention, it is a cDNA sequence encoding the specific iodine transporter (Na+/I− Symporter) NIS of human origin.

The adenoviruses used in the context of the present invention are recombinant adenoviruses, that is to say which comprise a heterologous DNA sequence. Advantageously, they are defective recombinant adenoviruses, that is to say adenoviruses incapable of autonomous replication in the target cells.

For the construction of the adenoviruses according to the invention, various serotypes may be used. There are indeed numerous serotypes, whose structure and properties vary somewhat, but which exhibit a comparable genetic organization. More particularly, the recombinant adenoviruses may be of human or animal origin. As regards the adenoviruses of human origin, there may be preferably mentioned those classified in group C, in particular adenoviruses type 2 (Ad2), 5 (Ad5), 7 (Ad7) or 12 (Ad12). Among the various adenoviruses of animal origin, there may be preferably mentioned the adenoviruses of canine origin, in particular all the strains of CAV2 adenoviruses [manhattan or A26/61 strain (ATCC VR-800) for example]. Other adenoviruses of animal origin are cited in particular in application WO 94/26914.

The genome of the adenoviruses comprises in particular an inverted terminal repeat sequence (ITR) at each end, an encapsidation sequence (Psi), early genes and late genes. The main early genes are contained in the E1, E2, E3 and E4 regions. Among these, the genes contained in the E1 region in particular are necessary for viral propagation. The main late genes are contained in the L1 to L5 regions. The genome of the Ad5 adenovirus has been completely sequenced and is accessible on data base (see in particular Genbank M73260). Likewise, portions, or even the whole of other adenoviral genomes (Ad2, Ad7, Ad12, and the like) have also been sequenced.

As indicated above, the adenoviruses according to the invention are defective and therefore incapable of autonomously replicating in the target cell. To this effect, various constructs derived from adenoviruses have been prepared, incorporating various therapeutic genes. In each of these constructs, the adenovirus was modified so as to render it incapable of replicating in the infected cell. Thus, the constructs described in the prior art are adenoviruses from which there has been deleted the E1 region, which is essential for viral replication, into which heterologous DNA sequences are inserted (Levrero et al., Gene 101 (1991) 195; Gosh-Choudhury et al., Gene 50 (1986) 161). Moreover, to improve the properties of the vector, it has been proposed to create other deletions or modifications in the genome of the adenovirus. Thus, a heat-sensitive point mutation was introduced into the ts125 mutant, making it possible to inactivate the 72kDa DNA-binding protein (DBP) (Van der Vliet et al., J. Virol. 1975, 15(2) 348-354). Other vectors comprise a deletion of another region essential for viral replication and/or propagation, the E4 region. The E4 region is indeed involved in regulating the expression of the late genes, in the stability of the late nuclear RNAs, in the extinction of the expression of the proteins of the host cell and in the efficiency of the replication of the viral DNA. Adenoviral vectors in which the E1 and E4 regions have been deleted therefore possess a transcriptional background noise and an expression of viral genes which are greatly reduced. Such vectors have been described for example in applications WO 94/28152, WO 95/02697, WO 96/22378. In addition, vectors carrying a modification in the IVa2 gene have also been described (WO 96/10088).

In a preferred embodiment of the invention, the recombinant adenovirus is a group C human adenovirus. More preferably, it is an Ad2 or Ad5 adenovirus.

Advantageously, the recombinant adenovirus used in the context of the invention comprises a deletion in the E1 region of its genome. More particularly still, it comprises a deletion of the E1a and E1b regions. By way of example, there may be mentioned deletions affecting nucleotides 454-3328, 386-3446, 459-3510 or 357-4020 (with reference to the genome of Ad5).

According to another variant, the recombinant adenovirus used in the context of the invention is defective for all or part of the E1 and E3 regions at least.

According to another variant, the recombinant adenovirus used in the context of the invention comprises, in addition to a deletion in the E1 region, a deletion affecting all or part of the E4 region of its genome. More particularly, the deletion in the E4 region affects all the open phases. There may be mentioned, by way of precise example, the deletions 33466-35535 or 33093-35535 or only part of the E4 region (ORF6 or ORF3 for example), as described in applications WO 95/02697 and WO 96/22378.

It may be, for example, so-called 3rd generation recombinant adenoviruses, that is to say which are defective for the E1 and E4 regions, as a whole or in part, and optionally for the E3 region. Particular variants of the invention consist of the use of adenoviruses carrying deletions affecting all or part of the following functional regions:

E1, E4 and E3,
E1, E4 and E2,
E1, E4, E2 and E3,
the above regions as well as all or part of the genes encoding the late adenovirus functions (L1 to L5), or alternatively,
all the coding viral regions.

As regards the adenoviruses additionally lacking late functions ("minimum" vector) or all the coding regions ("gutless" vector), their construction has been described for example by Parks et al. PNAS 93 (1996) p. 13565 and Lieber et al., J. Virol. 70 (1996) p. 8944.

This may also include hybrid adenoviral vectors such as those described in application WO99/60144 and in which the adenovirus is used as a vector for another virus and in particular as retrovirus vector.

The expression cassette containing the nucleic acid encoding the iodine transporter (NIS) may be inserted at different sites of the recombinant genome. It may be inserted in the E1, E3 or E4 region as a replacement for the deleted sequences or in addition. It may also be inserted at any other site, outside the sequences necessary in cis for the production of the viruses (ITR sequences and encapsidation sequence).

For the purposes of the present invention, the expression "expression cassette" for a nucleic acid is understood to mean a DNA fragment which may be inserted into a vector at specific restriction sites; the DNA fragment comprises, in addition to the nucleotide sequence encoding an RNA or a polypeptide of interest, the sequences necessary for the expression (enhancer(s), promoter(s), polyadenylation sequence and the like) of said sequence of interest. The DNA fragment and the restriction sites are designed to ensure insertion of said fragment into an appropriate reading frame for transcription and/or translation.

The recombinant adenoviruses are produced in an encapsidation line, that is to say a line of cells capable of complementing in trans one or more of the functions deficient in the recombinant adenoviral genome. Among the encapsidation lines known to persons skilled in the art, there may be mentioned for example the 293 line into which part of the adenovirus genome has been integrated. More precisely, the 293 line is a human embryonic kidney cell line containing the left end (about 11-12%) of the genome of the serotype 5 adenovirus (Ad5), comprising the left ITR, the encapsidation region, the E1 region, including E1a and E1b, the region encoding the pIX protein and part of the region encoding the pIVa2 protein. This line is capable of transcomplementing recombinant adenoviruses defective for the E1 region, that is to say which lack all or part of the E1 region, and of producing viral stocks having high titres. This line is also capable of producing, at permissive temperature (32° C.) stocks of virus comprising, in addition, the heat-sensitive E2 mutation. Other cell lines capable of complementing the E1 region have been described, based in particular on human lung carcinoma cells A549 (WO 94/28152) or on human retinoblasts (Hum. Gen. Ther. (1996) 215). Moreover, lines capable of transcomplementing several adenovirus functions have also been described. In particular, there may be mentioned lines complementing the E1 and E4 regions (Yeh et al., J. Virol. Vol. 70 (1996) pp. 559-565; Cancer Gen. Ther. 2 (1995) 322; Krougliak et al., Hum. Gen. Ther. 6 (1995) 1575) and lines complementing the E1 and E2 regions (WO 94/28152, WO 95/02697, WO 95/27071) or lines derived therefrom which can be used for producing minimum adenoviruses, in particular because they express, in addition, a site-specific recombinase activity involved in the construction of such viruses.

The recombinant adenoviruses may also be modified in the structure of the capsid in order to increase the efficiency of infection at the level of the tumor. For example, the capsid may contain a uPAR ligand or an RGD motif which allows targeting of the adenovirus to the tumor cells, such vectors and targeting sequences have been described in particular in application WO 00/12738. The targeting sequences may be inserted into the hexon protein or into the fibre protein. Preferably, the targeting sequences are inserted at the level of the deletion of the protein of the fibre or of the hexon. There are advantageously deleted from the polypeptide sequence of the hexon 13 amino acids corresponding to positions 279 to 292 of the polypeptide sequence of the hexon of Ad 5. There are advantageously deleted from the polypeptide sequence of the fibre 11 amino acids corresponding to positions 539 to 547 of the polypeptide sequence of the fibre (HI Loop) of Ad 5.

The recombinant adenoviruses are usually produced by introducing the viral DNA into the encapsidation line, followed by lysis of the cells after about 2 or 3 days (the kinetics of the adenoviral cycle being 24 to 36 hours). For the implementation of the method, the viral DNA introduced may be the complete recombinant viral genome, optionally constructed in a bacterium (WO 96/25506) or in a yeast (WO 95/03400), infected into the cells. It may also be a recombinant virus used to infect the encapsidation line. The viral DNA may also be introduced in the form of fragments each carrying part of the recombinant viral genome and a homologous region which makes it possible, after introduction into the encapsidation cell, to reconstitute the recombinant viral genome by homologous recombination between the various fragments. After lysing the cells, the recombinant viral particles may be isolated by any known technique such as cesium chloride gradient centrifugation or chromatography. An alternative method has been described in application WO 98/00528.

Sequences for regulating expression. The gene encoding the specific iodine transporter ($Na^+/I^-$ Symporter, NIS) may be placed under the control of any sequence for regulating expression such as for example a promoter or a promoter/enhancer, which is functional and which allows expression in the host tumor cells.

The sequences for regulating expression may comprise, in addition to the promoter region, a region situated in 3' of the gene encoding the specific iodine transporter and which provides a signal for termination of transcription and a polyadenylation site. All these elements constitute an expression cassette.

The promoter may be constitutive or regulatable (inducible). It may be the actual promoter of the gene. It may also include sequences of a different origin (which are responsible for the expression of other proteins, or even a synthetic promoter). In particular, it may include promoter sequences of eukaryotic or viral genes. For example, it may include promoter sequences derived from the genome of the cell which it is desired to transfect. Likewise, it may include promoter sequences derived from the genome of a virus, including of the virus used. In this regard, there may be mentioned for example the promoters E1A, MLP, CMV, RSV-LTR, MT-1, SV40 and the like.

In addition, these expression sequences may be modified by the addition of activation or regulatory sequences allowing tissue-specific or predominant expression in certain tissues (enolase promoter GFAP, and the like). It may indeed be particularly advantageous to use expression signals which are active specifically or predominantly in the tumor cells, so that the therapeutic gene is expressed or produces its effect only when the virus has effectively infected a tumor cell. The specific or predominant character of the expression means that the activity of the promoter is significantly much higher in the tumor cells. Although a non-specific expression can exist in other cells, the corresponding level of activity generally remains very low (negligible) compared with that observed in the tumor cells, generally lower by a factor of at least 10.

Among the promoters which can be used in the context of the invention, there may be mentioned the ubiquitous promoters (HPRT, vimentin, α-actin, tubulin, and the like), the promoters of the intermediate filaments (desmin, neurofilaments, keratin, GFAP), the promoters of genes of therapeutic interest (MDR, CFTR, factor VIII and the like), the tissue-specific promoters (promoters of the genes for desmin, myosins, creatine kinase, phosphoglycerate kinase), the promoters which are more specifically active in growing cells or alternatively the promoters corresponding to a stimulus such as the promoters corresponding to the natural hormones (steroid hormone receptors, retinoic acid receptors, and the like) or a promoter regulated by antibiotics (tetracycline, rapamycin, and the like) or other promoters corresponding to other molecules of natural or synthetic origin or promoter sequences derived from the genome of a virus such as the cytomegalovirus CMV enhancer/promoter, the retrovirus LTR promoter, the SV40 promoter, the promoter of the E1A gene, the MLP promoter. The promoters which can be regulated by tetracycline and the CMV promoter have been described in WO 96/01313, U.S. Pat. No. 5,168,062 and U.S. Pat. No. 5,385,839.

Among the promoters which can be used for carrying out the invention, there may be mentioned in particular the cytomegalovirus (CMV) promoter, the SV40 early promoter region (Benoist and Chambon, 1981, Nature 290:304-310), the promoter included in the Rous sarcoma virus 3' LTR region (Yamamoto, et al., 1980, Cell 22:787-797), the herpesvirus thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); the promoters of prokaryotic origin such as the β-lactamase promoter (VIIIa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); also see "Useful proteins from recombinant bacteria" in Scientific American, 1980, 242:74-94; the yeast promoters such as the Gal4, ADC (alcohol dehydrogenase), PGK (phosphoglycerol kinase) and alkaline phosphatase promoters; and the transcriptional regulatory sequences of animal origin which exhibit tissue specificity and which are used for transgenic animals: the regulatory sequences of the elastase I gene which are active in the cells of the acini of the pancreas (Swift, 1984, Cell 38:639-646; Ornitz et al., 1986, Cold Spring Harbor Symp. Quant. Biol. 50:399-409; MacDonald, 1987, Hepatology 7:425-515); the sequences for regulating the gene [lacuna] insulin which are active in the beta cells of the pancreas (Hanahan, 1985, Nature 315:115-122), the sequences for regulating the expression of the immunoglobulins which are active in the lymphoid cells (Grosschedl et al., 1984, Cell 38:647-658; Adames et al., 1985, Nature 318:533-538; Alexander et al., 1987, Mol. Cell. Biol. 7:1436-1444), the regulatory sequence of the mouse mammary tumor virus which is active in the cells of the testicles and of the breast, the lymphocytes and the mastocytes (Leder et al., 1986, Cell 45:485-495), the regulatory sequence of the PSA gene which is active in prostatic tumors, the regulatory sequence of the albumin gene which is active in the liver (Pinkert et al., 1987, Genes and Devel. 1:268-276), the regulatory sequence of the alpha-fetoprotein gene which is active in the liver (Krumlauf et al., 1985, Mol. Cell. Biol. 5:1639-1648; Hammer et al., 1987, Science 235:53-58), the regulatory sequence of the alpha 1-antitrypsin gene which is active in the liver (Kelsey et al., 1987, Genes and Devel. 1:161-171), the regulatory sequence of the β-globin gene which is active in myeloid cells (Mogram et al., 1985, Nature 315:338-340; Kollias et al., 1986, Cell 46:89-94), the regulatory sequence of the gene for basic myelin which is active in the oligodendrocytes in the brain (Readhead et al., 1987, Cell 48:703-712), the regulatory sequence of the gene for myosin light chain 2 which is active in the skeletal muscle (Sani, 1985, Nature 314:283-286), and the regulatory sequence of the gene for the gonadotrophin-releasing hormone which is active in the hypothalamus (Mason et al., 1986, Science 234:1372-1378).

In a specific embodiment of the invention, a defective recombinant adenovirus is used which comprises a gene encoding the specific iodine transporter (Na$^+$/I$^-$ Symporter) NIS under the control of a viral promoter, preferably chosen from RSV-LTR or the CMV early promoter.

It is also possible to combine the introduction of the NIS gene with the vector according to the invention with the introduction of a biological system which makes it possible to increase the biological half-life of iodine-131. It is thus possible to simultaneously or successively deliver into the tumor cells the NIS gene and a gene or several genes encoding polypeptides involved in an iodine organification system. There may be mentioned, for example, genes encoding polypeptides involved in a peroxidase system such as the gene encoding glucose oxidase. There may also be mentioned the gene encoding thyroperoxidase, an enzyme in the thyroid cells involved in the iodine organification process (Nucleic Acids Res. 15:6735-6735 (1987): sequence GenBank g37251). The introduction of the gene encoding thyroperoxidase may also be combined with the introduction of nucleic sequences encoding all or part of thyroglobulin (parts of thyroglobulin rich in tyrosin residues).

It is also possible to envisage delivering into the tumor cells the NIS gene and a gene or several genes encoding polypeptides involved in an iodine organification system by means of a single vector expressing several transgenes or by coinfection of two vectors, an adenoviral vector expressing the NIS gene and another vector, the viral or plasmid vector, expressing one or more genes encoding polypeptides involved in an iodine organification system.

It is, in addition, possible to combine the introduction of the NIS gene with the vector according to the invention with the administration of a system allowing a slowing down of the iodine efflux by a pharmacological agent (for example a lithium salt).

According to another variant, it is also possible to envisage combining the introduction of the NIS gene with other genes of therapeutic interest for the treatment of cancers. This may include a suicide gene such as the gene for the Herpes thymidine kinase or the gene for cytosine deaminase. It may include genes encoding proteins inducing apoptosis such as p53, Bax, BclX-s, Bad or any other antagonist of Bcl2 and BclX-1. This may include genes encoding variants of these proteins exhibiting improved properties such as a variant of p53 (CTS-1, WO 97/04092). This may also include genes encoding anti-angiogenic or angiostatic factors such as in particular the ligand for Tie-1 and Tie-2, angiostatin, endostatin, ATF factor, plasminogen derivatives, endothelin, thrombospondins 1 and 2, PF-4, interferon α or β, interleukin 12, TNFα, urokinase receptor, flt1, KDR, PAI1, PAI2, TIMP1, prolactin fragment. This may also include genes encoding proteins capable of inducing antitumor immunity or of stimulating immune response (IL2, GM-CSF, IL12, and the like). Among the genes encoding proteins of therapeutic interest in the treatment of cancers, it is also important to emphasize antibodies, variable fragments of single chain antibodies (ScFv) or any other antibody fragment possessing recognition capacities for use in immunotherapy for the treatment of tumors: anti-RAS antibodies (WO 9429446).

Advantageously, this may include a gene whose expression causes radiosensitization of tumor cells such as the p53 gene.

The administration of these genes or of the combination of two or more of these abovementioned genes of therapeutic interest may be carried out by introducing one or more of these genes into the adenoviral vector comprising the gene encoding the NIS transporter or into a separate vector of viral or nonviral nature.

According to another variant, the vector according to the invention may be administered in combination with an anti-cancer agent such as in particular taxol, taxoter and other taxoids [as described in particular in U.S. Pat. Nos. 4,857,653; 4,814,470; 4,924,011; 5,290,957; 5,292,921; 5,438,072; 5,587,493; EP 0 253 738; and WO 91/17976, WO 93/00928, WO 93/00929 and WO 9601815], or other therapeutic anti-cancer agents such as cis-platin and derivatives of platinum, etoposide and etoposide phosphate, bleomycin, mitomycin C, CCNU, doxorubicin, daunorubicin, idarubicin, ifosfamide, and the like.

The invention also relates to a pharmaceutical composition comprising an adenoviral vector as described above and a physiologically acceptable vehicle. The pharmaceutical compositions of the invention are preferably in an injectable form and may be formulated for intratumoral administration or for administration by the oral, parenteral, intranasal, intraarterial, intravenous or intratracheal route, and the like.

Preferably, the pharmaceutical composition contains pharmaceutically acceptable vehicles for a formulation intended to be administered by the intratumoral route.

The compositions according to the invention may comprise variable doses of recombinant adenoviruses, which can be easily adjusted by persons skilled in the art according to the applications envisaged and various parameters, and in particular according to the mode of administration used or alternatively the duration of the expression desired. In general, the recombinant viruses according to the invention are formulated and administered in the form of doses of between $10^4$ and $10^{14}$ pfu, and preferably $10^6$ to $10^{11}$ pfu. The term pfu ("plaque forming unit") corresponds to the infectivity of the virus, and is determined by infecting an appropriate cell culture, and measuring the number of infected cell plaques. The techniques for determining the pfu titre of a viral solution are well documented in the literature.

In addition, the compositions according to the invention may also comprise a chemical or biochemical transfer agent. The term "chemical or biochemical transfer agent" is understood to mean any compound (i.e. other than a recombinant virus) facilitating the penetration of a nucleic acid into a cell. This may include cationic nonviral agents such as cationic lipids, peptides, polymers (polyethyleneimine, polylysine), nanoparticles; or noncationic nonviral agents such as noncationic liposomes, polymers or noncationic nanoparticles.

According to a preferred embodiment, the compositions according to the invention comprise a defective recombinant vector comprising a gene encoding the iodine transporter NIS and are formulated for intratumoral administration. Advantageously, the compositions of the invention comprise from $10^4$ and $10^{15}$ pfu, and preferably $10^7$ to $10^{12}$ pfu.

The subject of the invention is also a method for preparing a medicament useful for preventing, improving and/or treating tumors characterized in that a recombinant vector comprising a nucleic acid encoding an iodine transporter (NIS) is mixed with one or more compatible and pharmaceutically acceptable adjuvants.

The invention also relates to a method for treating tumors in mammals, and in particular in humans, comprising the administration of an effective quantity of a defective recombinant adenovirus vector comprising a nucleic acid encoding the iodine transporter (NIS).

The term "effective quantity" designates a quantity sufficient to reduce by at least approximately 15%, preferably by at least 50%, and preferably still by at least 90% the volume of the tumors, and more preferably still a quantity sufficient to eliminate the tumors when the administration of the adenovirus comprising a nucleic acid encoding the iodine transporter (NIS) is combined with a metabolic radiotherapy treatment with iodine-135.

The invention relates to the treatment of tumors and more particularly the treatment of solid tumors. Among the solid tumors which may be treated by the subject of the invention, there may be mentioned in particular sarcomas and carcinomas, and by way of nonlimiting example, fibrosarcomas, osteogenic sarcomas, angiosarcomas, endotheliosarcomas, lymphangiosarcomas, Ewing tumors, colon cancer, pancreatic cancer, ovarian cancer, prostate cancer, adenocarcinomas, carcinomas of the kidney, liver or bile duct, Wilm's tumor, cervical cancer, testicular cancer, lung cancer, non-small-cell lung cancer, bladder cancer, epithelial carcinomas, gliomas, astrocytomas, melanomas, neuroblastomas and retinoblastomas.

The invention also relates to the prevention and/or treatment of proliferated disorders (such as metaplasias and displasias) of the epithelial tissues such as the epithelium of the cervix, of the oesophagus and of the lungs. In this regard, the invention relates to the treatment of conditions known or suspected to precede a progression to a neoplasia or a cancer, in particular in states where the growth of non-neoplastic cells such as hyperplasia, metaplasia and more particularly displasia occurs (for a review of these abnormal growth conditions, see Robbins and Angell, 1976, Basic Pathology, 2nd Ed., W.B. Saunders Co., Philadelphia, pp. 68-79). Hyperplasia is a form of controlled cell proliferation involving an increase in the number of cells in an organ, without significant structural or functional alteration of this organ. For example, a hyperplasia of the endometrium may precede cancer of the endometrium. Metaplasia is a controlled form of cell growth in which a type of adult or completely differentiated cell becomes substituted for another type of cell. Metaplasia may occur in epithelial tissues or in conjunctive tissues. Displasia is often an early warning sign of cancer and is found mainly in the epithelium; it is the most frequent form of neoplastic cell growth, involving the loss of uniformity of the individual cells and the loss of the structural orientation of the cells. Displasia typically occurs when a chronic irritation or inflammation exists, and is often observed in the cervix, the respiratory tracts, the vocal cavity, and on the bladder wall. For a review, see Fishman et al., 1985, Medicine, 2nd Ed., J.B. Lippincott Co., Philadelphia.

The present invention will be described in greater detail with the aid of the following examples which should be considered as illustrative and nonlimiting.

LEGEND TO THE FIGURES

FIG. 1: Diagram of the plasmid pAB1, of the plasmid pXL3048 and of the plasmid pAB2. The plasmid pXL3048 comprises the left end of the adenovirus type 5 genome (nucleotides 1-382), a polylinker comprising three unique cloning sites and part of the pIX gene (nucleotides 3446-4296). The plasmid pAB2 results from the cloning of the SspI-EcoRV fragment of pAB1 into pXL3048 previously linearized with EcoRV.

Figure 2:
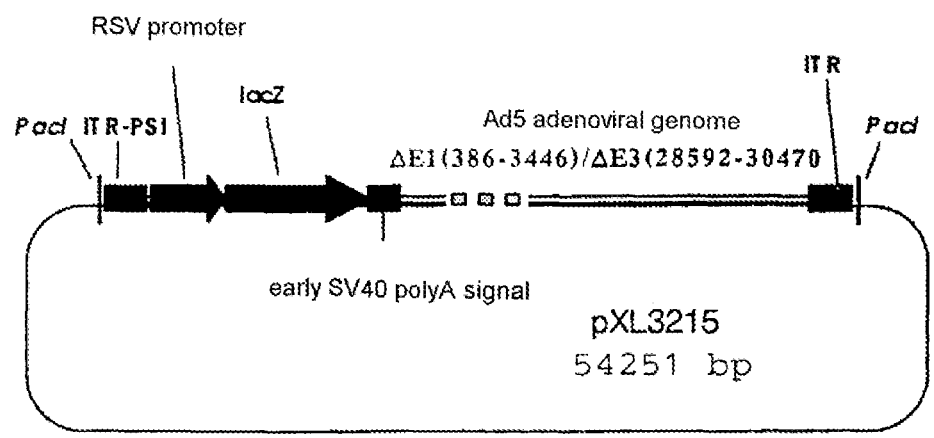
Figure 2:
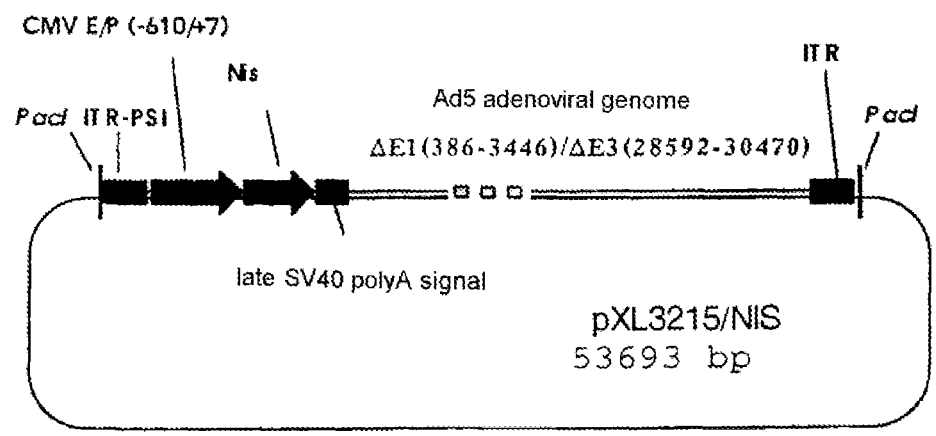

FIG. 2: Production of the plasmid pXL3215 generated by double recombination from the plasmids pAB2 and pXL3215 according to the method described by Crouzet et al. (PNAS vol. 94, p 1414, 1997). The plasmid pXL3215 contains the adenovirus type 5 genome deleted for the E1 and E3 region and contains the NIS expression cassette.

Figure 3:
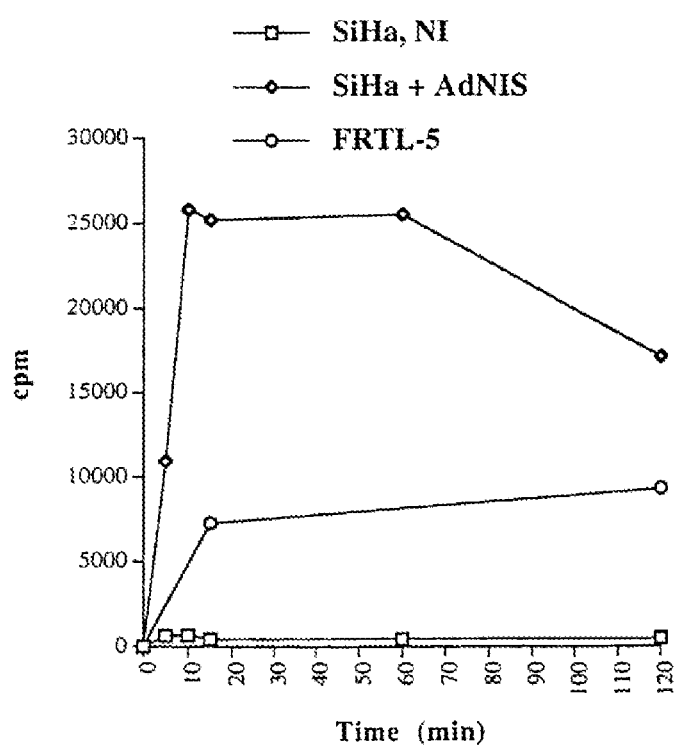

FIG. 3: Kinetics of accumulation of iodine-125 by the FTRL-5 and SiHa cells infected with the Ad-NIS vector (multiplicity of infection 10). The results of the kinetics are expressed as number of counts per minute per $10^6$ cells. The determination of the number of cells per well at the time of contact with iodine is the mean of two measurements.

Figure 4:
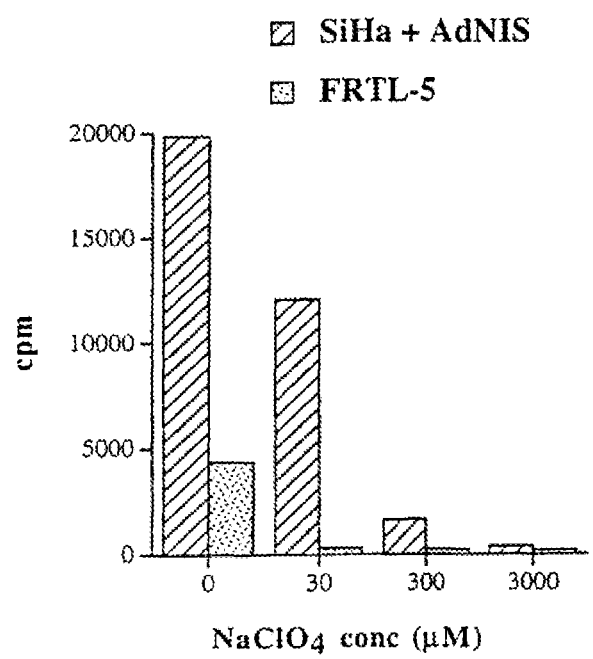

FIG. 4: Specific inhibition of the transport of iodine by NIS in the presence of perchlorate ($NaClO_4$) 30, 300 and 3000 µM. The contact time between the cells and iodine-125 is 15 minutes.

Figure 5A:
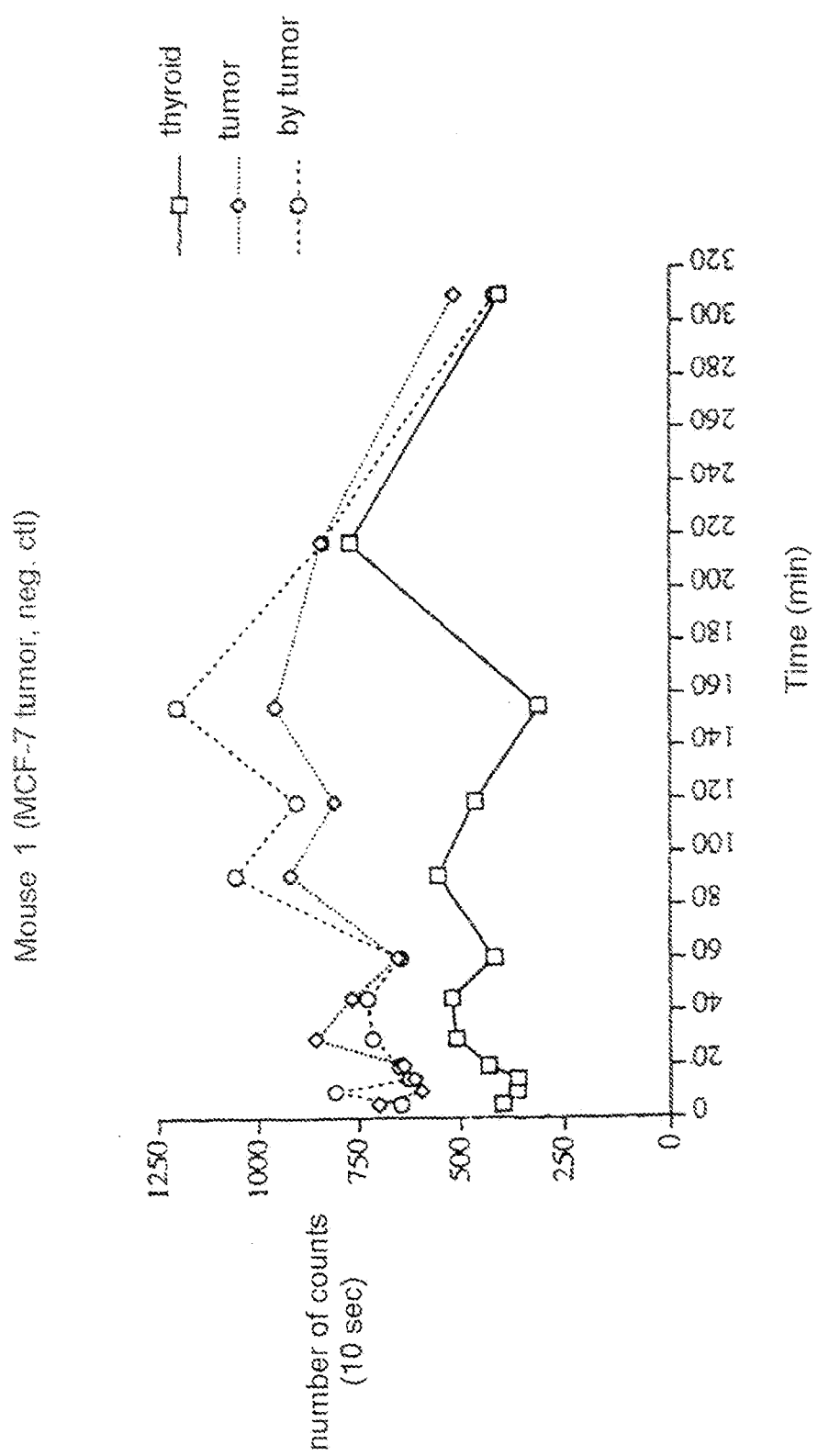
Figure 5B:
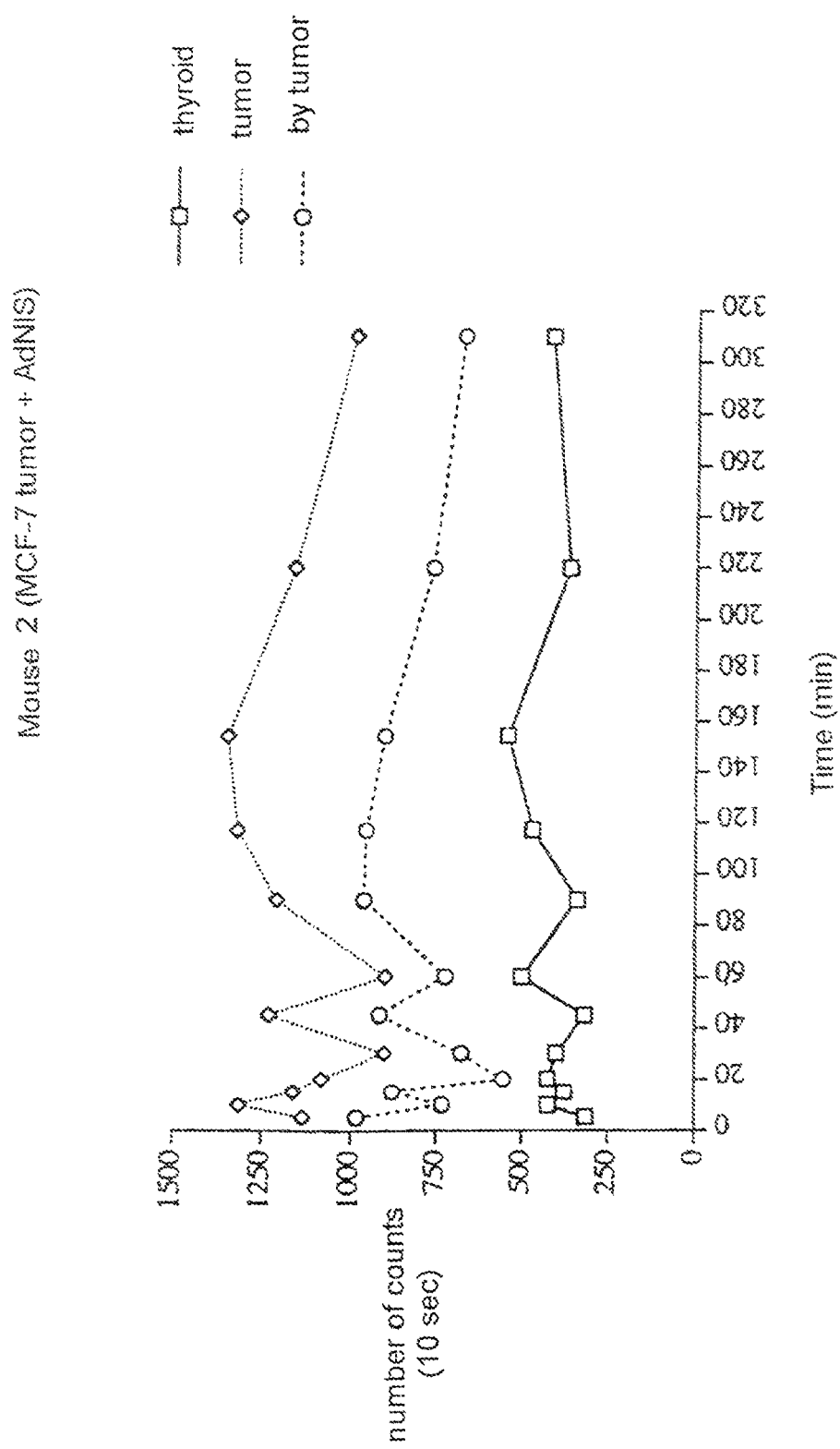

FIG. 5: Accumulation of iodine in vivo by tumors infected with the Ad-NIS vector. The MCF-7 cells (human tumor cells of mammary cancer) were injected subcutaneously into nude mice ($5 \times 10^6$ cells). After 15 days (start of appearance of the tumors), daily intraperitoneal injections of thyroxin (2 µg/animal/day) were carried out for 15 days. The Ad-CMV-NIS vector was then injected into certain animals by the intratumoral route ($2 \times 10^9$ pfu/tumor; size of the tumors 3-6 mm). Three days after the infection, 6 µCi of $^{126}I$ are injected into mice by the intraperitoneal route. The countings were carried out over 10 seconds at regular time intervals by placing the probe over the thyroid, over the tumor, and immediately near the tumor. The results are expressed as number of counts detected (measurement over 10 seconds) as a function of time.

Figure 6:
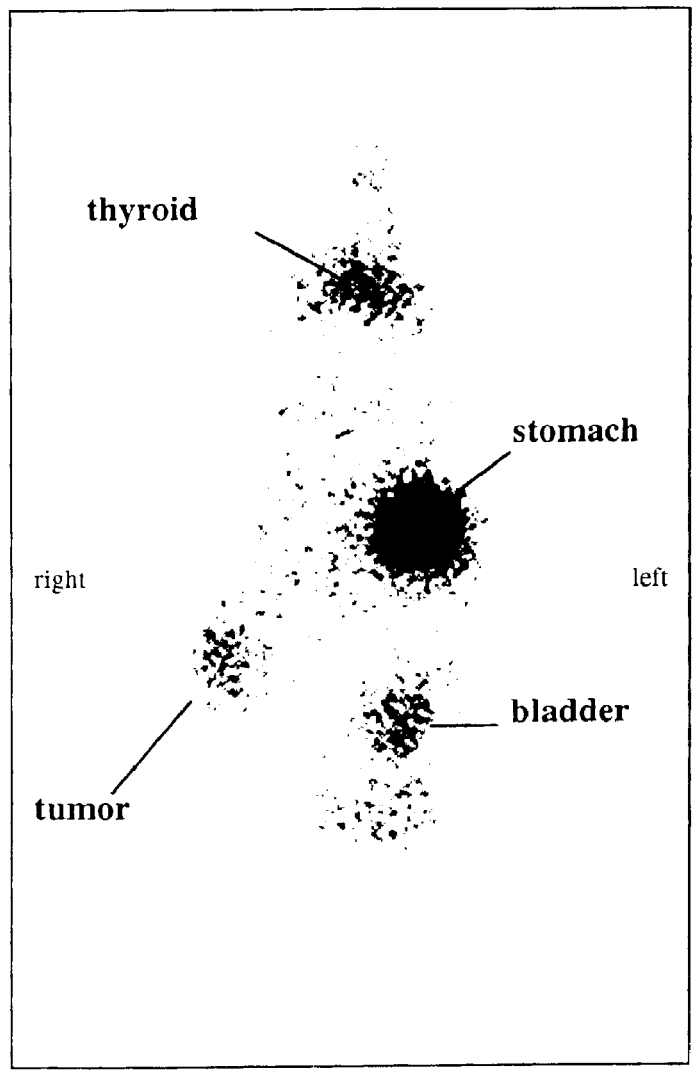

FIG. 6: Scintigraphy for a mouse whose tumor was infected with the Ad-NIS vector. The MCF-7 cells (human tumor cells, mammary cancer) were injected subcutaneously into nude mice ($5 \times 10^6$ cells). After 15 days (start of appearance of the tumors), daily intraperitoneal injections of thyroxine (2 μg/animal/day) were carried out for 15 days. The Ad-NIS vector was then injected by the intratumor route ($2 \times 10^9$ pfu/tumor; size of the tumors 3-6 mm). Three days post-infection, 50 μCi of $^{123}$I are injected by the intraperitoneal route into the mice. The countings are carried out 1 hour after injection of iodine. The image is a ventral view of the animal.

MATERIALS AND METHODS

General Molecular Biology Techniques

The methods conventionally used in molecular biology such as preparative extractions of plasmid DNA, centrifugation of plasmid DNA in cesium chloride gradient, agarose or acrylamide gel electrophoresis, purification of DNA fragments by electroelution, extractions of proteins with phenol or with phenol-chloroform, precipitation of DNA in saline medium with ethanol or isopropanol, transformation in *Escherichia coli*, and the like, are well known to persons skilled in the art and are abundantly described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

For the ligations, the DNA fragments may be separated according to their size by agarose or acrylamide gel electrophoresis, extracted with phenol or with a phenol/chloroform mixture, precipitated with ethanol and then incubated in the presence of T4 phage DNA ligase (Biolabs) according to the supplier's recommendations.

The filling of the protruding 5' ends may be carried out with the Klenow fragment of DNA polymerase I of *E. coli* (Biolabs) according to the supplier's specifications. The destruction of the protruding 3' ends is carried out in the presence of T4 phage DNA polymerase (Biolabs) used according to the manufacturer's recommendations. The destruction of the protruding 5' ends is carried out by a controlled treatment with S1 nuclease.

Mutagenesis directed in vitro by synthetic oligodeoxynucleotides may be carried out according to the method developed by Taylor et al. [Nucleic Acids Res. 13 (1985) 8749-8764] using the kit distributed by Amersham.

The enzymatic amplification of DNA fragments by the so-called PCR technique [Polymerase-catalyzed Chain Reaction, Saiki R. K. et al., Science 230 (1985) 1350-1354; Mullis K. B. and Faloona F. A., Meth. Enzym. 155 (1987) 335-350] may be carried out using a "DNA thermal cycler" (Perkin Elmer Cetus) according to the manufacturer's specifications.

The verification of the nucleotide sequences may be carried out by the method developed by Sanger et al. [Proc. Natl. Acad. Sci. USA, 74 (1977) 5463-5467] using the kit distributed by Amersham.

EXAMPLES

Example 1

Construction of a Defective Recombinant Adenovirus Expressing the Gene Encoding the Specific Iodine Transporter ($Na^+/I^-$ Symporter) NIS This example describes the construction of a defective adenoviral vector carrying the gene encoding the specific iodine transporter ($Na^+/I^-$ Symporter) NIS (ref Genbank U60282) operably linked to the CMV promoter.

The fragment comprising nucleotides 74 to 2046 of the sequence of the rat nis gene (Dai et al., 1996, Nature 379: 458-460) was cloned in the form of an AatII-HindIII fragment into the PvuII-HindIII sites of the plasmid pCEP-4 (Invitrogen). The AatII site of the AatII-HindIII fragment was previously made blunt by treating with Mung Bean nuclease (Biolabs) before insertion into the plasmid pCEP-4. The resulting plasmid is called pAB1.

The plasmid pAB1 (FIG. 1) comprises the nis gene whose expression is placed under the control of the cytomegalovirus CMV enhancer/promoter (nucleotides −522 to +72) (Boshart et al. 1985, Cell, 41: 521-530) and followed by the SV40 virus polyadenylation site (nucleotides 2538 to 2759 according to the SV40 genome, Genbank locus SV4CG).

The combination formed by (i) the cytomegalovirus enhancer/promoter, (ii) the cDNA of the nis gene and (iii) the SV40 virus polyadenylation site is called hereinafter the NIS expression cassette.

The SspI-EcoRV fragment (3711 bp) of the plasmid pAB1 comprising the NIS expression cassette defined above is then cloned into the shuttle vector pXL3048 previously linearized with EcoRV. The resulting vector is called pAB2 (FIG. 2). The plasmid pXL3048 is a plasmid derived from the plasmid Kan-SacB (Crouzet et al., PNAS vol. 94, p. 1414-1419, 1997) comprising the left end of the type 5 adenovirus genome (nucleotides 1-382), a polylinker comprising three unique cloning sites and part of the pIX gene (nucleotides 3446-4296).

The adenovirus Ad-NIS was constructed according to the method described by Crouzet et al., (PNAS vol. 94, p. 1414-1419, 1997) by homologous recombination between the plasmid pAB2 and the plasmid pXL3215.

The plasmid pXL3215 contains the genome of an adenovirus containing an RSV-LacZ cassette inserted into its E1 region (ΔE1 386-3446) and a deletion in the E3 region (ΔE3 28592-30470).

The principle of the construction is described in FIG. 2. The plasmid pXL3215 generated by this double recombination contains the genome of a type 5 adenovirus deleted for the E1 and E3 region and containing the CMV-NIS-poly A SV40 expression cassette. This construct is verified by sequencing of the NIS expression cassette.

The Ad-NIS adenovirus is generated by infection of the DNA of pXL3215 digested with PacI into the 293 line (ATCC CRL-1573). The viral particles obtained are then amplified in this same line and stocks of viruses produced are purified by double CsCl gradient.

The viral particles are then used to study the expression of the NIS gene in various tumor lines.

Example 2

Accumulation of Iodine In Vitro by Tumor Cells Infected with the Ad-NIS Vector

The capacity for accumulating iodine in the cells infected with the Ad-NIS vector was tested in various lines: the epithelial tumor cells SiHa (ATCC HTB-35), mammary tumor cells MCF7 (ATC HTB-22) and T-47D (ATCC HTB-133) and tumor cells of prostatic origin DU-145 (ATCC HTB-81) and PC-3 (ATCC CRL-1435).

The cells are infected with the Ad-NIS vector at a multiplicity of infection of 10. The capacity of the cells to capture iodine is tested 28 to 29 h after infection according to the Weiss et al. method [Endocrinology (1984) 114: 1090-1098]. The infected cells are washed with HBSS buffer and placed in contact for the time indicated in FIG. 3 with 0.5 ml of HBSS buffer containing 0.1 µCi of iodine-125. At the end of the contact time, the cells are washed once with cold HBSS buffer and then incubated for 20 min with cold ethanol. The quantity of iodine-125 captured by the cells is determined by assaying the radioactivity of the ethanol, with a gamma counter.

The results obtained with the SiHa line are presented in FIG. 3 and may be compared with those obtained with the FRTL-5 cells (rat thyroid cells which capture iodine naturally and which serve as control).

The specific inhibition of iodine transport by NIS was tested in the presence of perchlorate. $NaClO_4$ was added to the HBSS buffer containing iodine-125 so as to obtain final concentrations of 30, 300 and 3000 µM. The contact time between the cells and the iodine-125 is 15 minutes. The results are presented in FIG. 4. The results are expressed as number of counts for the same number of cells.

The FRTL-5 cells (positive control) fix a certain quantity of iodine, and it is observed that this phenomenon is very rapid (maximum nearly reached after 15 min of contact). The results obtained show that the SiHa cells (human epithelial tumor cells) which are not infected do not capture iodine. Surprisingly, it is observed that the SiHa cells infected with the Ad-NIS vector capture up to 5 times more iodine than the FRTL-5 cells. It is also noted that the initial kinetics of the phenomenon is comparable to that observed for the FRTL-5 cells. The specificity of the transfer was confirmed by infection with a control adenovirus not containing the nis gene (result not presented).

The results of the inhibition experiments (FIG. 4) show that the fixing of iodine in the FRTL-5 cells is inhibited at more than 90% from an $NaClO_4$ concentration of 30 µM (93% for 30 µM, 95% at high concentrations). It is of interest to note that, on the other hand, for the SiHa cells infected with Ad-NIS, the concentration of inhibitor required in order to obtain the same level of inhibition is much higher (only 40% inhibition for 30 µM $NaClO_4$, 92% inhibition for 300 µM $NaClO_4$ and 98% for 3 mM $NaClO_4$).

The inhibition experiment makes it possible to conclude that the capacity of the SiHa cells infected with Ad-NIS to capture iodine is indeed due to the expression NIS in these cells, since the phenomenon is inhibited by $NaClO_4$ which is a competitive and specific inhibitor of the transport of iodide ions by NIS. Similar results were obtained for other human tumor cell lines (mammary tumor cells: MCF-7 and T47-D, and tumor cells of prostatic origin: DU-145 and PC-3).

The results relating to the inhibition by $NaClO_4$ also confirm that the infection of tumor cells with Ad-NIS leads to a particularly high level of expression of NIS, since high $NaClO_4$ concentrations are required to inhibit the phenomenon (in the case of SiHa cells and relative to the FRTL-5 cells, an inhibitor concentration which is 10 times higher is required to obtain the same level of inhibition).

All these results demonstrate that the adenoviral vector is a particularly advantageous vector for the transfer of the nis gene and that the use of such a vector makes it possible to obtain a level of accumulation of iodine in nonthyroid tumor cells of the order of 5 times greater than that observed for the cells which naturally capture iodine-125.

Example 3

Accumulation of Iodine In Vivo by Tumors Infected with the Ad-NIS Vector

MCF-7 cells (human tumor cells of mammary cancer) were injected subcutaneously into nude mice ($5 \times 10^6$ cells). After 15 days (start of appearance of the tumors), daily intraperitoneal injections of thyroxin (2 µg/animal/day) were carried out for 15 days, so as to allow the thyroid of the animals to rest. The Ad-NIS vector was then injected into certain animals by the intratumor route ($2 \times 10^9$ pfu/tumor); the diameter of the tumors at the time of injection was 3 to 6 mm. Three days after the infection, 6 µCi of $^{125}I$ were injected into mice by the intraperitoneal route, and counts were carried out over 10 seconds with the aid of a probe which can be moved to different sites on the animal. Counts were carried out at regular time intervals by placing the probe over the thyroid, over the tumor, and immediately near the tumor. The results are presented in FIG. 5. The results are expressed as number of counts detected (measurement over 10 seconds) as a function of time.

In the control animals (without administration of Ad-NIS), the thyroid fixes a small quantity of iodine, but by virtue of the treatment with thyroxine, no substantial accumulation of iodine in the thyroid is observed over time. No fixing of iodine in the tumor is observed in the control animals (see FIG. 5A). The fact that NIS is naturally present in the stomach, and the fact that iodine is eliminated in the urine explain the relatively high values observed (relatively high background noise).

The animals treated with Ad-NIS administered by the intratumor route (FIG. 5B) exhibit no substantial accumulation of iodine in the thyroid (effect of the treatment with thyroxine). On these animals, the quantities of iodine detected by placing the probe on the tumor are systematically higher than the quantity of iodine detected near the tumor, which indicates that there is indeed fixing of iodine in the tumor after treatment with the Ad-NIS vector.

To confirm the fixing of iodine in the tumors, measurements of radioactivity by scintigraphy were carried out on the animals treated with the Ad-NIS vector. The results obtained are presented in FIG. 6. The animals used were prepared according to the protocol described above, except that 50 µ/Ci of $^{123}I$ were injected by the intraperitoneal route; the image was obtained one hour after injection of iodine.

The image is a ventral view of the animal. Four iodine fixing regions are visible: the thyroid, the bladder (route for eliminating iodine), the stomach (in which NIS is naturally expressed) and the tumor. These scintigraphy results confirm the preceding results obtained by counting and show that the vectors according to the invention make it possible to obtain substantial fixing of iodine in the tumors.

Example 4

Quantitative Evaluation of the Accumulation of Iodine In Vivo by Tumors Infected with the Ad-NIS Vector SiHa cells ($5 \times 10^6$ cells) were injected subcutaneously into nude mice (n=12) on both flanks of the animal. After 15 days (start of appearance of the tumors), daily intraperitoneal injections of thyroxin (2µg/animal/day) were carried out for 15 days, so as to allow the thyroid of the animals to rest. For each animal, the Ad-NIS vector was then injected by the intratumoral route ($2\times10^9$ pfu/tumor) into a tumor; the other tumor serving as control; the diameter of the tumors at the time of injection was 5 to 8 mm. Three days after the infection, 6. μCi of $^{126}$I were injected into mice by the intraperitoneal route. The animals were sacrificed 90 minutes after the administration of $^{125}$I, and the quantity of $^{125}$I was determined. The results are presented in Table 1. The results are expressed as a percentage of $^{125}$I administered per gram of tissue.

| mouse | Tumor treated with Ad-NIS (% $^{125}$I administered/g of tissue) | Control tumor (% $^{125}$I administered/g of tissue) | ratio |
|---|---|---|---|
| 1 | 9.53 | 1.75 | 5.4 |
| 2 | 16.81 | 0.88 | 19.1 |
| 3 | 5.56 | 1.08 | 5.1 |
| 4 | 11.93 | 1.51 | 7.9 |
| 5 | 4.26 | 1.02 | 4.2 |
| 6 | 12.91 | 0.92 | 14.0 |
| 7 | 12.76 | 1.16 | 11.0 |
| 8 | 5.53 | 1.42 | 3.9 |
| 9 | 10.75 | 1.45 | 7.4 |
| 10 | 14.52 | 0.85 | 17.1 |
| 11 | 10.10 | 0.41 | 24.6 |
| 12 | 10.91 | 1.17 | 9.3 |
|  | 10.46 ± 3.79 | 1.14 ± 0.36 | 10.8 ± 6.6 |

The results obtained show that the tumors treated with the Ad-NIS vector are capable of accumulating iodine $^{125}$I very efficiently and up to 25 times more than in the untreated tumors. These results confirm the preceding results and show that the vectors according to the invention make it possible to obtain substantial fixing of iodine in the tumors.

The invention claimed is:

1. A method for treating and/or inhibiting the growth of tumors, comprising the administration of an effective quantity of a defective recombinant adenovirus, wherein the defective recombinant adenovirus comprises
   i) a promoter allowing expression in tumor cells wherein the promoter is selected from the group consisting of E1A, MLP, CMV and RSV-LTR, MT-1, SV40;
   ii) at least one DNA sequence encoding the specific human iodine transporter (Naf/I-Symporter) NIS comprising at least a deletion of all or part of the E1 region and -a deletion of all or part of the E4 region; and
   iii) at least one gene encoding a polypeptide involved in a peroxidase system such as the gene for glucose oxidase or for thyroperoxidase.

2. A method for treating and/or inhibiting the growth of tumors, comprising the administration of a pharmaceutical composition comprising defective recombinant adenoviruses that comprise:
   i) a promoter allowing expression in tumor cells wherein the promoter is selected from the group consisting of E1A, MLP, CMV and RSV-LTR, MT-1, SV40;
   ii) at least one DNA sequence encoding the specific human iodine transporter (Naf/I-Symporter) NIS comprising at least a deletion of all or part of the E1 region and -a deletion of all or part of the E4 region; and
   iii) at least one gene encoding a polypeptide involved in a peroxidase system such as the gene for glucose oxidase or for thyroperoxidase.

3. A method for treating and/or inhibiting the growth of tumors according to claim 2, wherein the pharmaceutical composition is in injectable form.

4. A method for treating and/or inhibiting the growth of tumors according to claim 3, wherein the pharmaceutical composition, characterized in that it comprises between $10^4$ and $10^{14}$ pfu/ml defective recombinant adenoviruses.

5. A method for treating and/or inhibiting the growth of tumors according to claim 4, wherein the pharmaceutical composition comprises between $10^6$ and $10^{11}$ pfu/ml defective recombinant adenoviruses.

6. A method for treating and/or inhibiting the growth of tumors according to claim 4, wherein the pharmaceutical composition comprises between $10^4$ and $10^7$ pfu/ml defective recombinant adenoviruses.

7. A method for treating and/or inhibiting the growth of tumors according to claim 4, wherein the pharmaceutical composition comprises between $10^4$ and $10^6$ pfu/ml defective recombinant adenoviruses.

* * * * *